United States Patent
Waters et al.

(10) Patent No.: US 11,957,319 B2
(45) Date of Patent: Apr. 16, 2024

(54) ENDOBRONCHIAL ULTRASOUND IMAGING

(71) Applicant: Verathon Inc., Bothell, WA (US)

(72) Inventors: Kendall R. Waters, Maple Valley, WA (US); Moira Galvin, Bothell, WA (US)

(73) Assignee: VERATHON INC., Bothell, WA (US)

( * ) Notice: Subject to any disclaimer, the term of this patent is extended or adjusted under 35 U.S.C. 154(b) by 349 days.

(21) Appl. No.: 16/682,054

(22) Filed: Nov. 13, 2019

(65) Prior Publication Data
US 2020/0178788 A1 Jun. 11, 2020

Related U.S. Application Data

(60) Provisional application No. 62/775,972, filed on Dec. 6, 2018.

(51) Int. Cl.
| | | |
|---|---|---|
| A61B 1/267 | (2006.01) | |
| A61B 1/00 | (2006.01) | |
| A61B 1/05 | (2006.01) | |
| A61B 5/00 | (2006.01) | |
| A61B 8/00 | (2006.01) | |

(52) U.S. Cl.
CPC ........ *A61B 1/2676* (2013.01); *A61B 1/00066* (2013.01); *A61B 1/00114* (2013.01); *A61B 1/05* (2013.01); *A61B 5/0033* (2013.01); *A61B 5/6853* (2013.01); *A61B 8/4483* (2013.01); *A61B 8/56* (2013.01); *A61B 2562/0204* (2013.01)

(58) Field of Classification Search
CPC ...... A61B 1/267–2676; A61B 1/00082; A61B 8/12; A61B 1/00105; A61B 1/00098
See application file for complete search history.

(56) References Cited

U.S. PATENT DOCUMENTS

| | | |
|---|---|---|
| 5,474,075 A | 12/1995 | Goldberg et al. |
| 2008/0183080 A1 | 7/2008 | Abraham |
| 2009/0187105 A1* | 7/2009 | Ichikawa ................. A61B 8/12 600/444 |

(Continued)

FOREIGN PATENT DOCUMENTS

| | | |
|---|---|---|
| EP | 3323351 A1 | 5/2018 |
| JP | 2017515620 A | 6/2017 |

(Continued)

*Primary Examiner* — Alexandra L Newton
(74) *Attorney, Agent, or Firm* — Snyder, Clark, Lesch & Chung, LLP

(57) ABSTRACT

An endobronchial ultrasound (EBUS) bronchoscope is configured as a single-use (e.g., disposable) device. The bronchoscope includes an insertion tube having a proximal section adjacent the handle and a distal tip. An ultrasound transducer assembly is located at the distal tip. The ultrasound transducer assembly includes an ultrasound transducer array, transmit-and-receive circuitry for the ultrasound transducer array, and a flexible interconnection between the ultrasound transducer array and the transmit-and-receive circuitry. The insertion tube further includes an imaging lumen including one or more power cables and one or more communication wires that extend from the ultrasound transducer assembly through the proximal section and a working channel that is separate from the imaging lumen.

18 Claims, 12 Drawing Sheets

(56) References Cited

U.S. PATENT DOCUMENTS

| | | |
|---|---|---|
| 2009/0292171 A1 | 11/2009 | Ito et al. |
| 2010/0041949 A1 | 2/2010 | Tolkowsky |
| 2011/0184238 A1 | 7/2011 | Higgins et al. |
| 2013/0053694 A1 | 2/2013 | Roschak et al. |
| 2014/0142389 A1* | 5/2014 | Lim .................. A61B 1/0052 600/147 |
| 2014/0276069 A1* | 9/2014 | Amble ............... A61B 8/4488 600/447 |
| 2015/0073267 A1 | 3/2015 | Brannan et al. |
| 2015/0305710 A1 | 10/2015 | Stigall et al. |
| 2016/0235305 A1 | 8/2016 | Wang et al. |
| 2016/0278626 A1* | 9/2016 | Cornhill ................. A61B 1/31 |
| 2016/0287210 A1 | 10/2016 | Chumo et al. |
| 2017/0071579 A1* | 3/2017 | Ko ..................... A61B 8/4483 |
| 2019/0069878 A1* | 3/2019 | Irie .................... A61B 8/4494 |
| 2020/0000439 A1* | 1/2020 | Satoh .................... A61B 8/56 |
| 2021/0007711 A1* | 1/2021 | Van Der Horst ........ A61B 8/12 |
| 2021/0251604 A1* | 8/2021 | Sudol .................. B06B 1/0622 |

FOREIGN PATENT DOCUMENTS

| | | |
|---|---|---|
| WO | 2008073560 A1 | 9/2002 |
| WO | 02096481 A2 | 12/2002 |
| WO | 2018141949 A1 | 8/2018 |

* cited by examiner

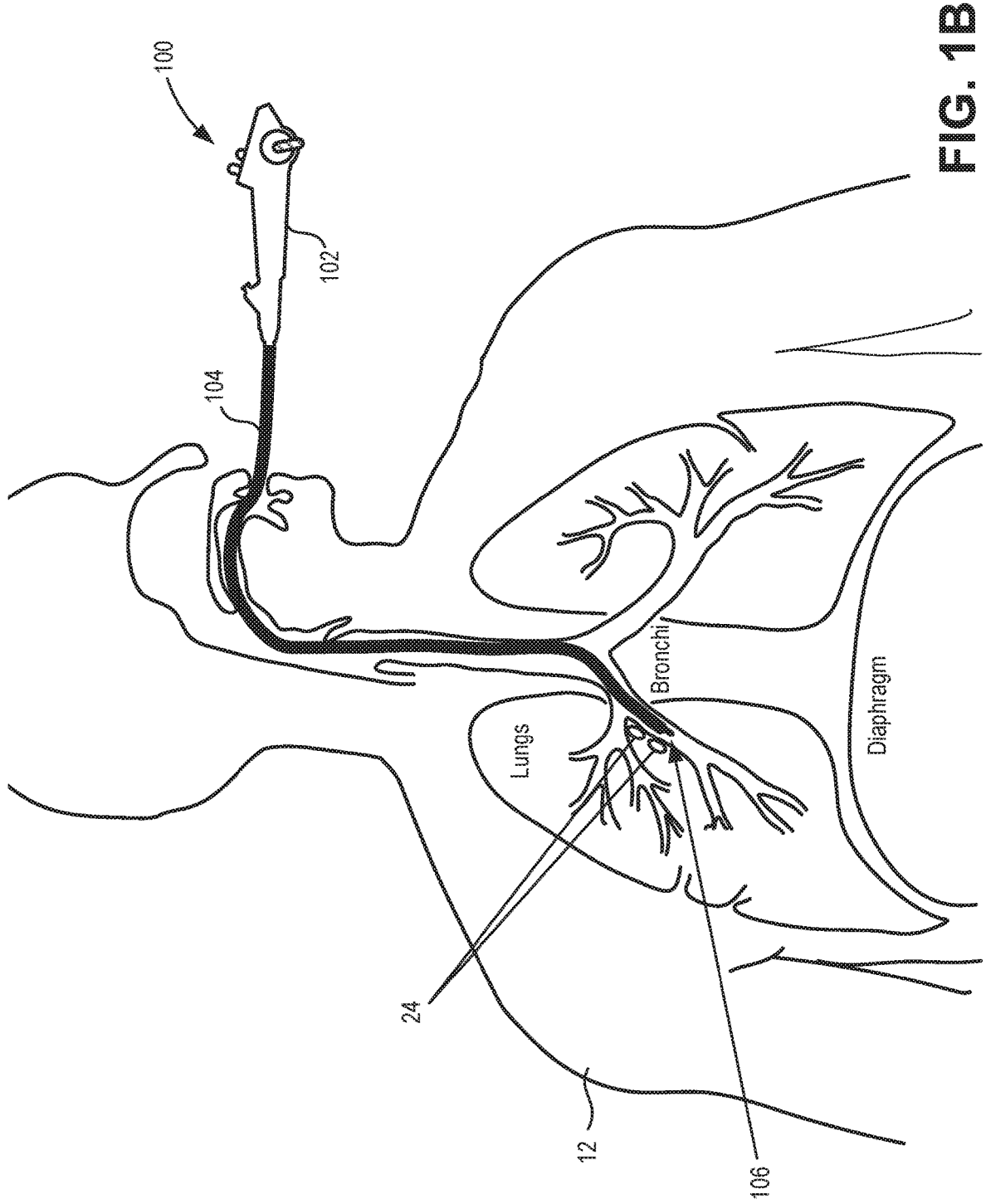

ENDOBRONCHIAL ULTRASOUND IMAGING

CROSS-REFERENCE TO RELATED APPLICATION

This application claims priority under 35 U.S.C. § 119, based on U.S. Provisional Patent Application No. 62/775, 972 filed Dec. 6, 2018, entitled "Endobronchial Ultrasound Imaging," the disclosure of which is hereby incorporated by reference.

BACKGROUND OF THE INVENTION

Physicians use endobronchial ultrasound (EBUS) techniques to guide lung cancer staging procedures. In particular, physicians use EBUS bronchoscopes to guide transbronchial needle aspiration (TBNA) of lymph nodes.

Currently available EBUS bronchoscopes are reusable. Healthcare facilities reprocess EBUS bronchoscopes between uses in different patients to minimize infection risks. A reliable, high-quality reprocessing program requires an infrastructure that involves administration, documentation, inventory control, physical facility maintenance, education, training, risk assessment, and quality assurance.

BRIEF DESCRIPTION OF THE DRAWINGS

FIG. 1B is a schematic of an endobronchial ultrasound (EBUS) bronchoscope inserted within a patient, according to an implementation described herein;

DETAILED DESCRIPTION OF THE PREFERRED EMBODIMENTS

The following detailed description refers to the accompanying drawings. The same reference numbers in different drawings may identify the same or similar elements.

Implementations described herein relate to an endobronchial ultrasound (EBUS) bronchoscope that can employed as a single-use (e.g., disposable) device. The EBUS bronchoscope may be used, for example, to image bronchial lymph nodes for lung cancer staging and to guide transbronchial needle aspiration (TBNA). The EBUS bronchoscope includes a microelectromechanical system (MEMS)-based ultrasound transducer. The transducer is curved to enable imaging a wider view, compared to a flat array. The transducer is integrated with analog and digital electronics installed within a distal tip of the EBUS bronchoscope. The arrangement requires fewer wires (e.g., compared to a conventional EBUS bronchoscope) and a correspondingly smaller diameter lumen extending through an insertion tube.

Figure 1A:
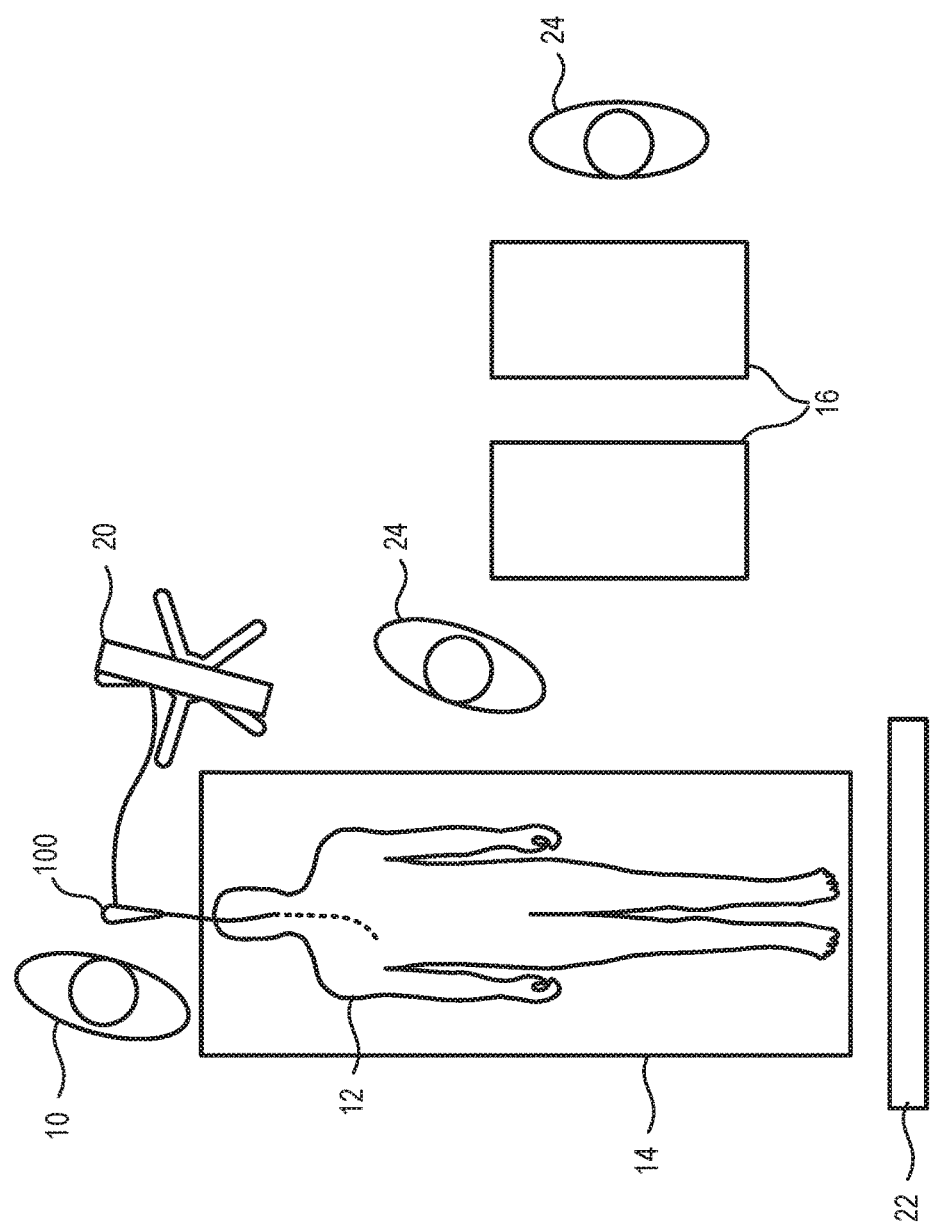
FIG. 1A is a schematic of an environment in which systems and methods described herein may be implemented.

FIG. 1A illustrates a top view of an exemplary use of EBUS technology by an operator 10 (e.g., a pulmonologist or pulmonary interventionist) for evaluation of the lungs of a patient 12. An interventional suite may include a patient table 14, one or more portable carts 16, a console 20, a display 22, and an EBUS bronchoscope 100. The patient 12 lies supine upon the patient table 14. The operator 10 is generally at one end of the patient table 14 toward the head of the patient 12. One or more assistants 24 may be present.

FIG. 1B is a cross-sectional view of the upper body of the patient 12 with a side view of EBUS bronchoscope 100 delivered to the bronchus of the patient 12. EBUS bronchoscope 100 includes a handle 102 connected to an insertion tube 104 that is inserted into the patient and directed to a region of interest. For example, a distal tip 106 of the EBUS bronchoscope 100 may be positioned in proximity to one or more bronchial lymph nodes 24.

Figure 2:
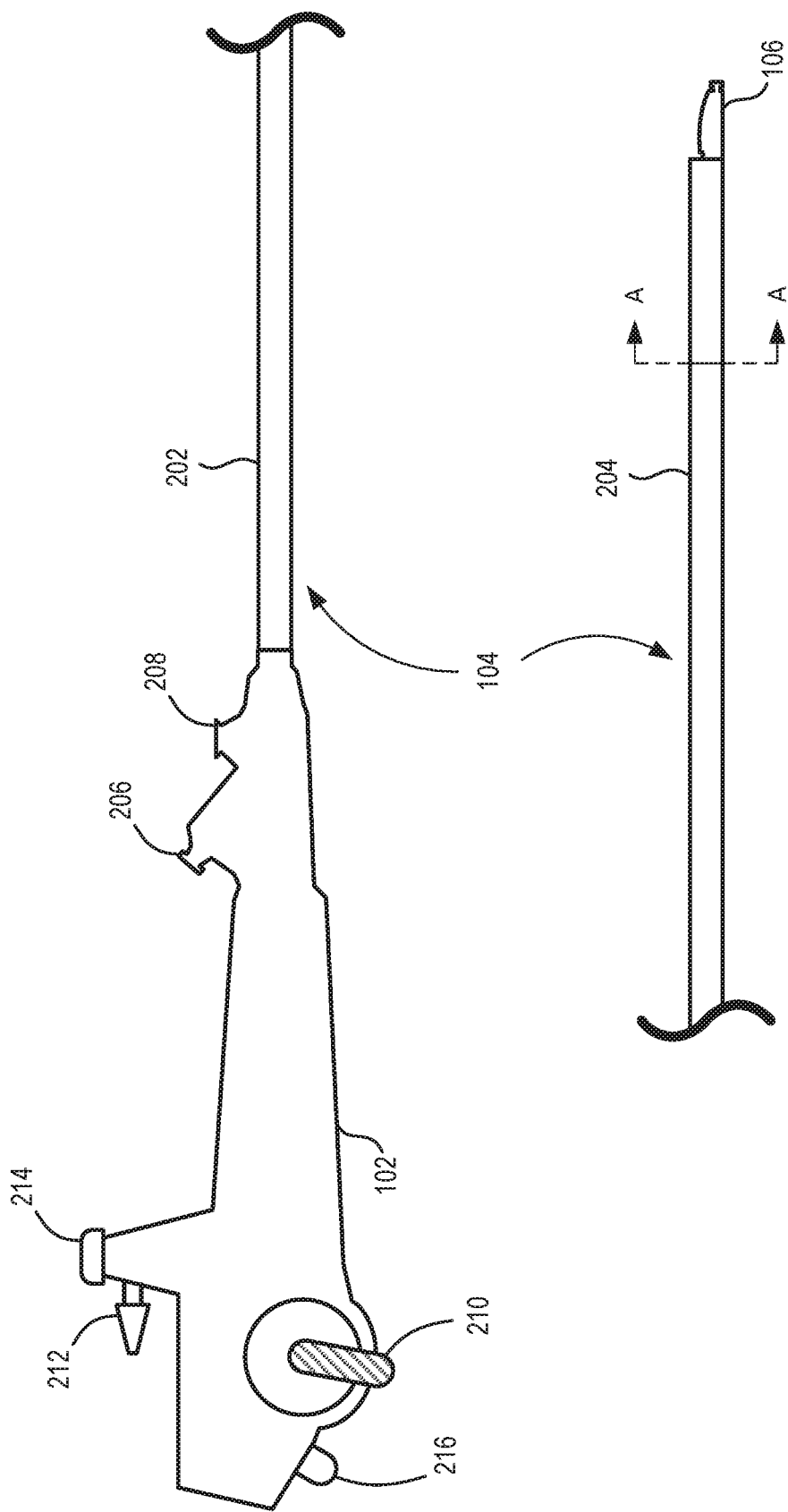
FIG. 2 is a schematic side view of the EBUS bronchoscope of FIGS. 1A and 1B.

FIG. 2 is a side view of EBUS bronchoscope 100, including handle 102, insertion tube 104, and distal tip 106. Insertion tube 104 may include a proximal section 202 that connects to handle 102 and a distal section 204 between proximal section 202 and distal tip 106. Handle 102 includes a working channel entry port 206, an injection port 208, and a suction port 212. Working channel entry port 206 may be used for inserting fluids or tools (e.g., a biopsy needle, etc.) into a working channel (e.g., working channel 302, FIG. 3) extending through insertion tube 104 and exiting near distal tip 106. Injection port 208 may be used to insert or extract fluid through a lumen (e.g., inflation lumen 408, FIG. 4) extending through insertion tube 104 to distal tip 106. Suction port 212 may also feed into the working channel (e.g., working channel 302) to provide suction through the working channel. Handle 102 also includes a series of controls, such as a flexion/extension lever 210, a suction button 214, and/or one or more image/video controls 216. The flexion/extension lever 210 controls wires within insertion tube 104 for steering distal tip 106 during insertion to a patient. The suction button 214 controls a valve adjacent to the suction port for purposes of controlling suction when suction port 212 is connected to a suction device. The image/video control(s) 216 can be used to take still and video images at distal tip 106 throughout the procedure. As described further herein, distal tip 106 includes an ultrasound transducer that enables visualization of the structure of bronchial walls and surrounding tissues (e.g., including bronchial lymph nodes 24).

Figure 3:
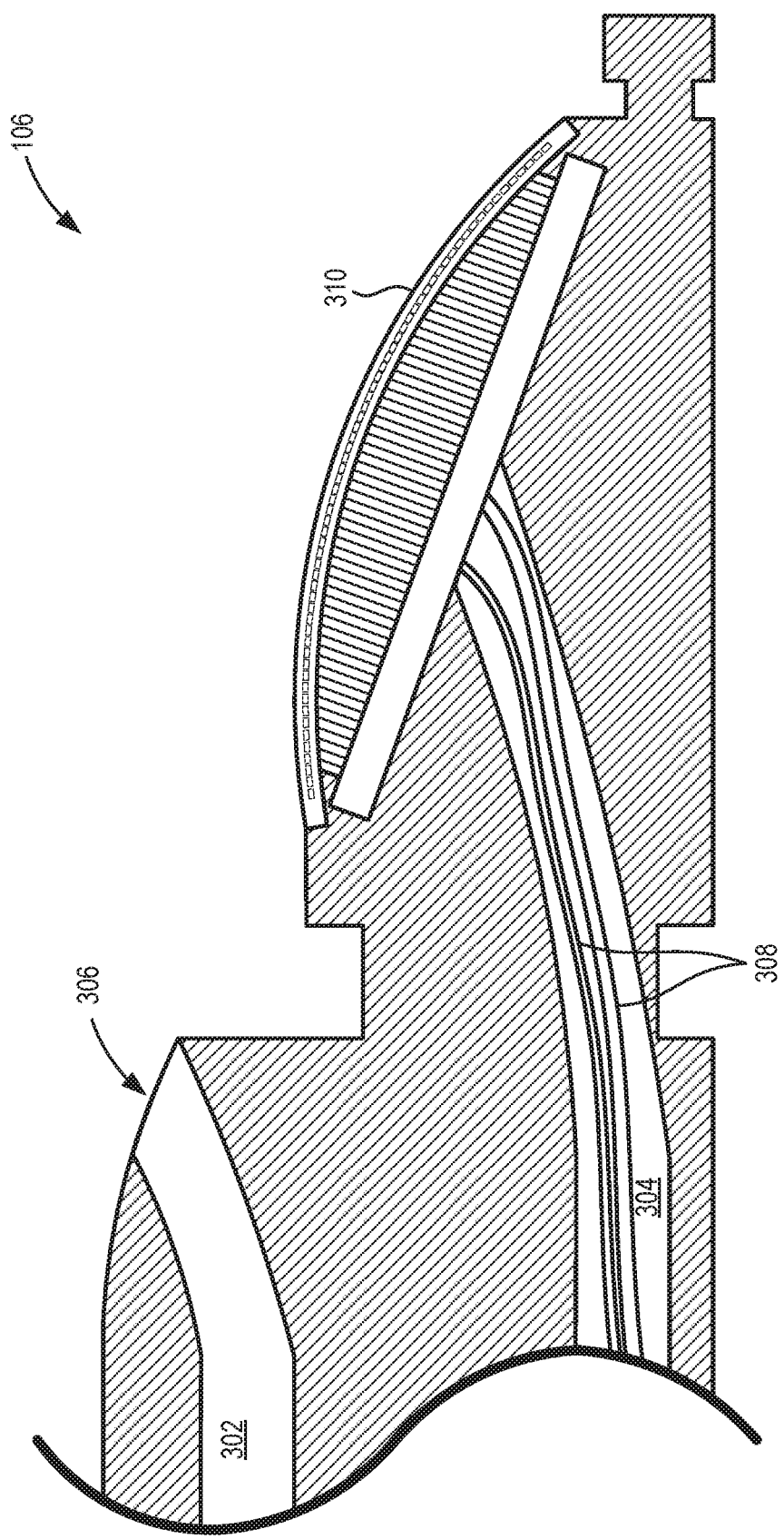
FIG. 3 is a longitudinal cross-sectional view of a distal tip of the EBUS bronchoscope of FIG. 2, according to one implementation.
Figure 4:
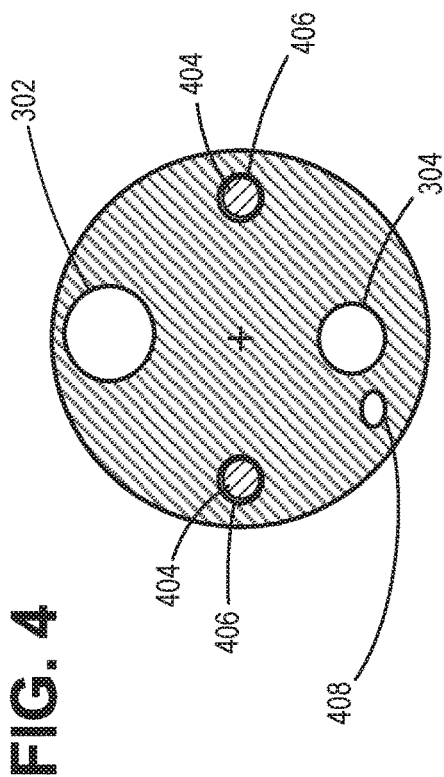
FIG. 4 is a cross-sectional end view of a portion of the EBUS of FIG. 2, according to an implementation described herein.
Figure 5:
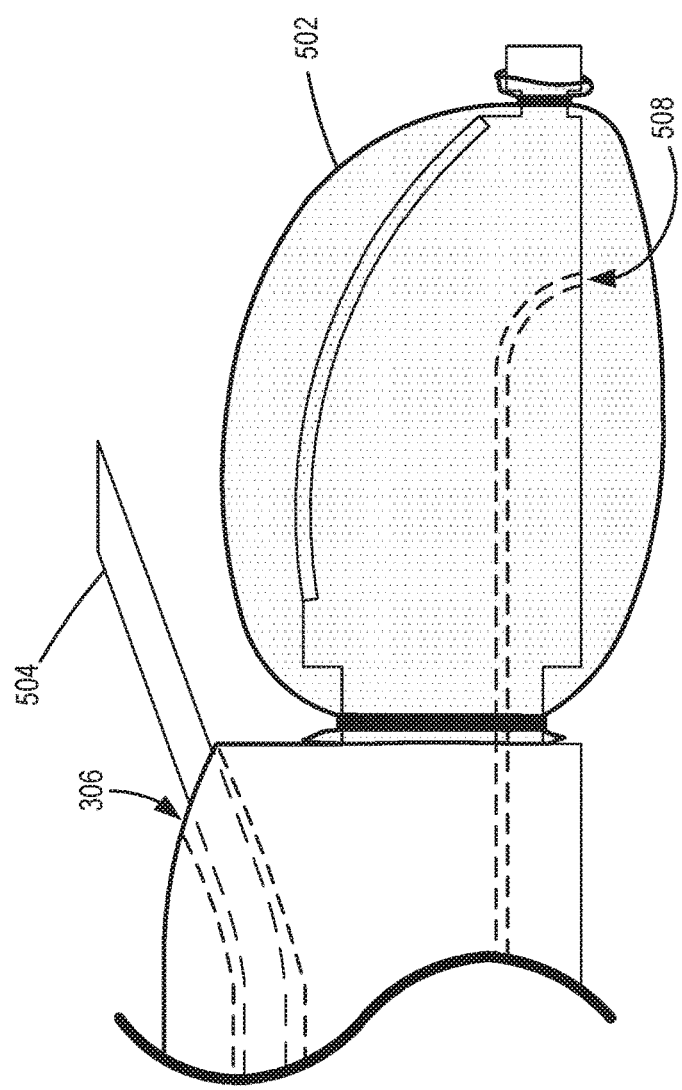
FIG. 5 is an illustration of a distal tip of an EBUS bronchoscope shown with a balloon and a biopsy needle according to one embodiment.

FIG. 3 is cross-sectional side view of distal tip 106, according to an implementation described herein. FIG. 4 is a cross-sectional end view of distal section 204 of insertion tube 104, shown along section A-A of FIG. 2. FIG. 5 is a side view of view distal tip 106, shown with a partially inflated balloon 502 installed and a biopsy needle 504 extending from working channel exit port 306. Referring collectively to FIGS. 3-5, insertion tube 104 includes working channel lumen 302, ultrasound (US) imaging core lumen 304, two flexion/extension cable lumens 406, and an inflation lumen 408. Generally, EBUS bronchoscope 100 is designed to enable delivery of the distal tip 106 to the bronchi (e.g., of patient 12), with good push-ability, torque-ability, and steer-ability to enable an operator to easily manipulate distal tip 106 to a desired location and orientation. Each of working channel lumen 302, US imaging core lumen 304, and inflation lumen 408 may extend from handle 102 to the general area of distal tip 106 along the axial length of insertion tube 104. Flexion/extension cable lumens 406 may extend substantially along the axial length of insertion tube 104, but not as far as distal tip 106.

Working channel lumen 302 may accommodate tools or fluids to perform procedures near distal tip 106. Working channel lumen 302 may join or connect with working channel entry port 206 in handle 102 to a working channel exit port 306 near distal tip 106. When distal tip 106 is positioned at a desired area within a patient, a tool (e.g., biopsy needle 504, forceps, etc.) with guidewires that is inserted at working channel entry port 206 may be pushed through working channel lumen 302 and exit through working channel exit port 306 to access a body part of the patient.

US imaging core lumen 304 may accommodate power and communication wires (referred to herein collectively as cables 308) to enable use of ultrasound transducer assembly 310. US imaging core lumen 304 may permit cables 308 from ultrasound transducer assembly 310 to extend back to handle 102, which may, in turn, connect cables 308 to console 20.

Transducer assembly 310 may include a MEMS-based ultrasound transducer with integrated analog and/or digital electronics installed at distal tip 106. The inclusion of integrated electronics within distal tip 106 minimizes the number of wires required to pass through US imaging core lumen 304, reducing material and assembly costs while allowing for the diameter of US imaging core lumen 304 to be minimized. Transducer assembly 310 is described further, for example, in connection with FIGS. 6-8 below.

Flexion/extension cable lumens 406 accommodate cables 404 extending from flexion/extension lever 210 (or another steering control) into distal section 204. The cables 404 may be used to steer/direct distal tip 106 of insertion tube 104 in the patient. According to another embodiment, flexion/extension lever 210, flexion/extension cable lumens 406 and cables 404 may be eliminated from EBUS bronchoscope 100, such as when a diameter of insertion tube 104 and distal tip 106 are small enough to be inserted within a working channel of a larger bronchoscope.

As shown in FIG. 5, in one implementation, EBUS bronchoscope 100 includes a balloon 502 that may be installed over a portion of distal tip 106, and particularly adjacent to ultrasound transducer assembly 310. Balloon 502 may include, for example, a sterile latex balloon that may be inflated when distal tip 106 is within the patient. According to one implementation, balloon 502 may be inflated with saline solution after insertion into the patient to prevent an air interface with the transducer array of ultrasound transducer assembly 310 during ultrasound scanning.

Inflation lumen 408 may provide a channel from injection port 208 in handle 102 to an outlet port 508 in distal tip 106. Outlet port 508 may be located anywhere within the portion of distal tip 106 that is encased by balloon 502. Inflation lumen 408 may provide a path for saline (or other fluid) to be inserted into and extracted from balloon 502. For example, a syringe at injection port 208 may be used to insert fluid through inflation lumen to balloon 502. In one implementation, such as when EBUS bronchoscope 100 (or insertion tube 104) is provided as single-use (e.g., disposable) device, EBUS bronchoscope 100 (or insertion tube 104) may be provided to practitioners (e.g., by a medical equipment provider) in sterile packaging with balloon 502 pre-installed over distal tip 106, thus reducing clinician preparation time. Similarly, in another implementation, EBUS bronchoscope 100 (or insertion tube 104) may be provided with an integrated biopsy needle 540 positioned within working channel lumen 302.

Figure 6:
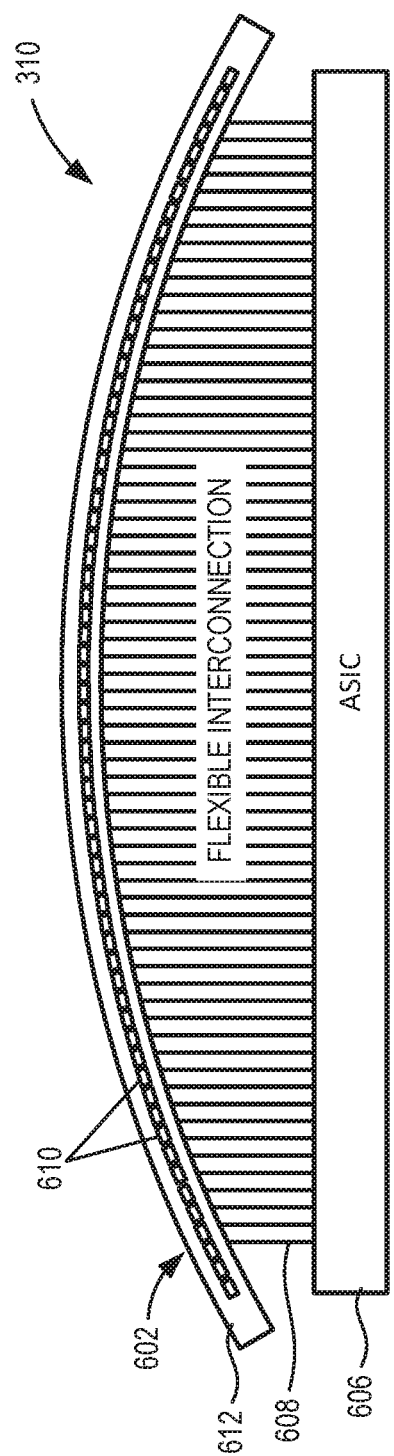
FIG. 6 is a side view of an ultrasound transducer array of the distal tip of FIG. 3.

FIG. 6 is a cross-sectional side view of transducer assembly 310. As shown in FIG. 6, transducer assembly 310 may include curved ultrasound transducer array 602, integrated signal processing electronics 606, and a flexible interconnection 608. Transducer array 602 may include multiple MEMS drums 610 mounted on a curved substrate 612. In one implementation, each of MEMS drums 610 may include a thin nitride membrane and top aluminum electrode suspended over a cavity. Generally, drums 610 are capacitive structures that operate under an applied electrostatic field. A signal voltage applied across the membrane varies the membrane tension and causes drums 610 to vibrate and emit ultrasonic waves. Conversely, during reception of ultrasound, an acoustic wave causes the membrane to move, altering the capacitance of the drums 610 and creating an output current.

Figure 7:
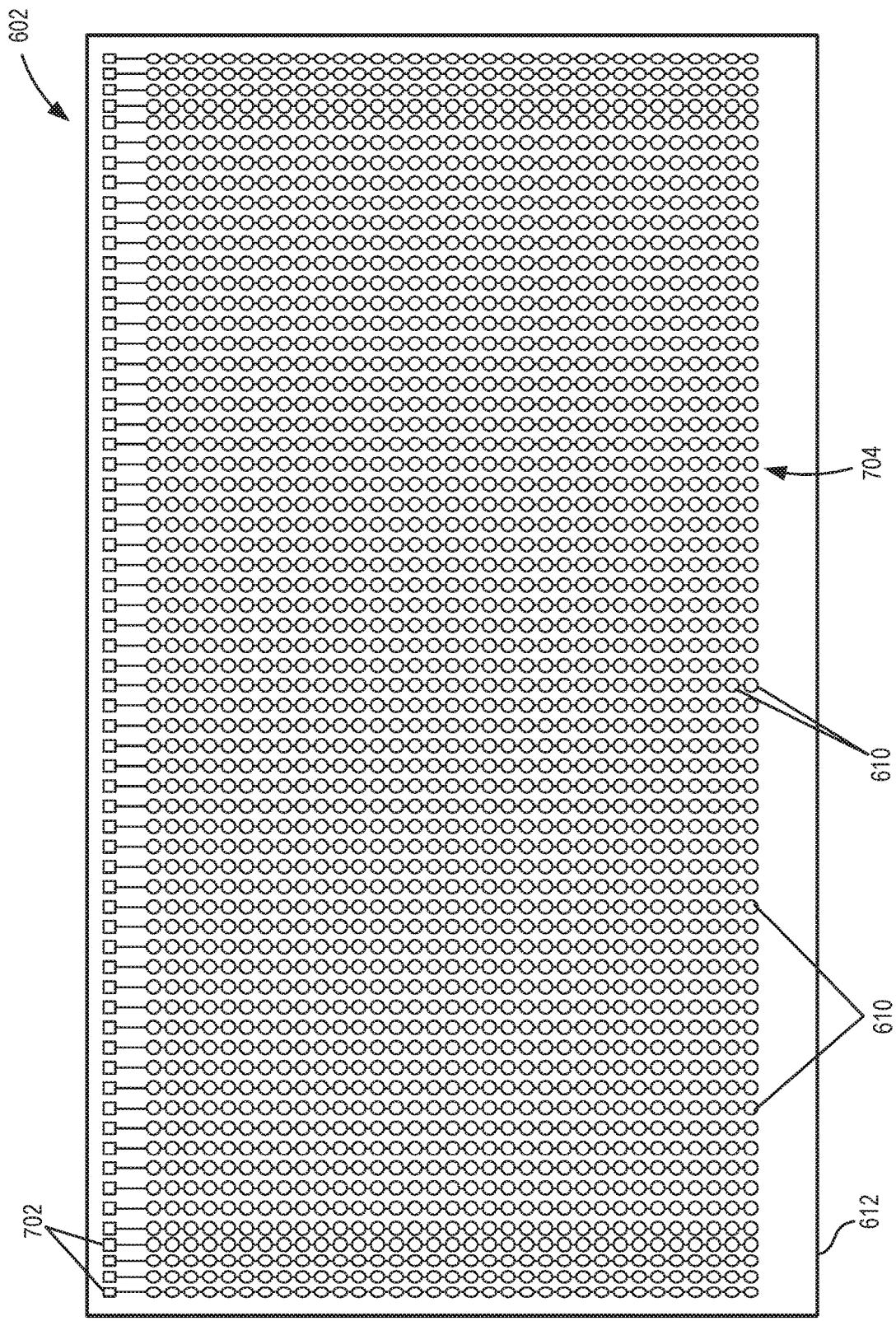
FIG. 7 is a top view of the ultrasound transducer array of FIG. 6.

FIG. 7 is a top view of curved ultrasound transducer array 602. As shown in FIG. 7, one or more MEMS drums 610 (such as a row of MEMS drums 610, as shown in FIG. 7) may be connected to electrodes 702. According to one implementation, transducer array 602 may be a MEMS-based ultrasound design, such as a capacitive micromachined ultrasound transducer (CMUT) or piezoelectric micromachined ultrasound transducer (PMUT). Transducer array 602 may include multiple elements 704. Each element 704 includes one or more MEMS drums 610 and an electrode 702 which are electrically connected. As shown in the example of FIG. 7, an element 704 may include a row of MEMS drums 610 connected to a single electrode 702. MEMS drums 610 act as transducer elements that transmit ultrasound energy and receive acoustic reflections or echoes generated by internal structures/tissue within the patient. Substrate 612 may be made of silicon, for example. The MEMS-based ultrasound transducer described herein may provide for integrated electronics and relatively low cost.

In the configuration of FIGS. 6 and 7, ultrasound transducer array 602 includes a two-dimensional curved array. The curve of ultrasound transducer array 602 is generally convex (e.g., curves outward) relative to the longitudinal axis of insertion tube 104. A curved array can provide a wider field of view than a typical flat array, which is important for ultrasound transducers having a limited aperture size. According to one implementation, the ultrasound transducer may have a nominal center frequency between 5 megaHertz (MHz) and 25 MHz. The nominal center frequency is approximately 7.5 MHz for imaging the major bronchi and may be greater than 10 MHz for imaging the peripheral bronchi. The orientation of transducer elements 704 may be stationary with respect to probe distal tip 106 so that a selected anatomical region may be scanned by selectively energizing elements 704 in the array 602.

Figure 8:
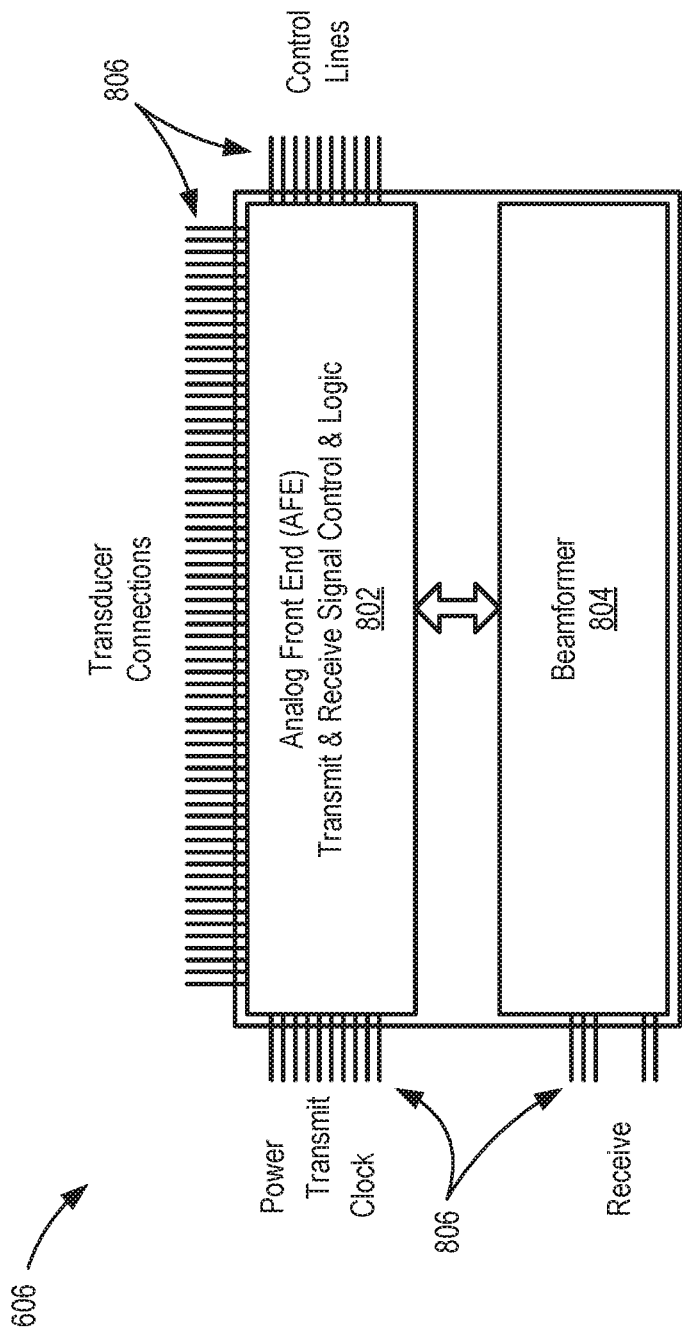
FIG. 8 is a block diagram of an application-specific integrated circuit (ASIC) of FIG. 6.

Signal-processing electronics 606 may be used to provide transmit-and-receive circuitry and/or beamforming logic for ultrasound transducer array 602 within distal tip 106. In one implementation, signal-processing electronics 606 may include an application-specific integrated circuit (ASIC). FIG. 8 is a functional block diagram of signal-processing electronics 606. As shown in FIG. 8, signal-processing electronics 606 may include an analog front end (AFE) 802, a beamformer 804, and connection lines 806. AFE 802 may include transmit-and-receive circuitry for ultrasound transducer array 602. AFE 802 may include, for example, a processor (e.g., a field-programmable gate array (FPGA), a reduced instruction set computing (RISC) microcontroller, etc.), a digital-to-analog converter (DAC), a transmitter (Tx) 420, a transmit/receive (T/R) switch, a multiplexer/demultiplexer (MUX/DEMUX), time-gain compensation (TGC) circuitry, and an analog-to-digital converter (ADC). AFE 802 may adjust the characteristics of ultrasound signals, such as the carrier frequency, acoustic intensity, pulse repeating frequency (PRF), signal bias, gain level, etc., in achieving the optimal performance for US transducer assembly 310.

Beamformer 804 may provide input to AFE 802 for controlling the phase and relative amplitude of signals to provide directional signal transmission or reception. Connection lines 806 may include connections for elements 704 of curved ultrasound transducer array 602 (e.g., corresponding to flexible interconnection 608), as well as power connection, transmit drive signal connections, clock signals, receive signals, and control lines. The arrangement of signal-processing electronics 606 as part of transducer assembly 310 within distal tip 106 may reduce the number and/or length of transmission lines typically required for an ultrasound transducer array. A reduction in number of transmission lines can reduce cost of EBUS bronchoscope 100.

Flexible interconnection 608 may provide wired connections between transducer array 602 and ASIC 606. In one implementation, flexible interconnection 608 may include an interconnect platform of high density wiring, such as FLEX-TO-RIGID (F2R) technology. Transducer array 602 may be fabricated on silicon wafers, transferred onto polyimide, and partially rendered flexible by means of a two-step backside silicon deep reactive ion etching. This flexibility allows for the transducer array 602 to be wrapped around distal tip 106 of insertion tube 104, for example.

Figure 9:
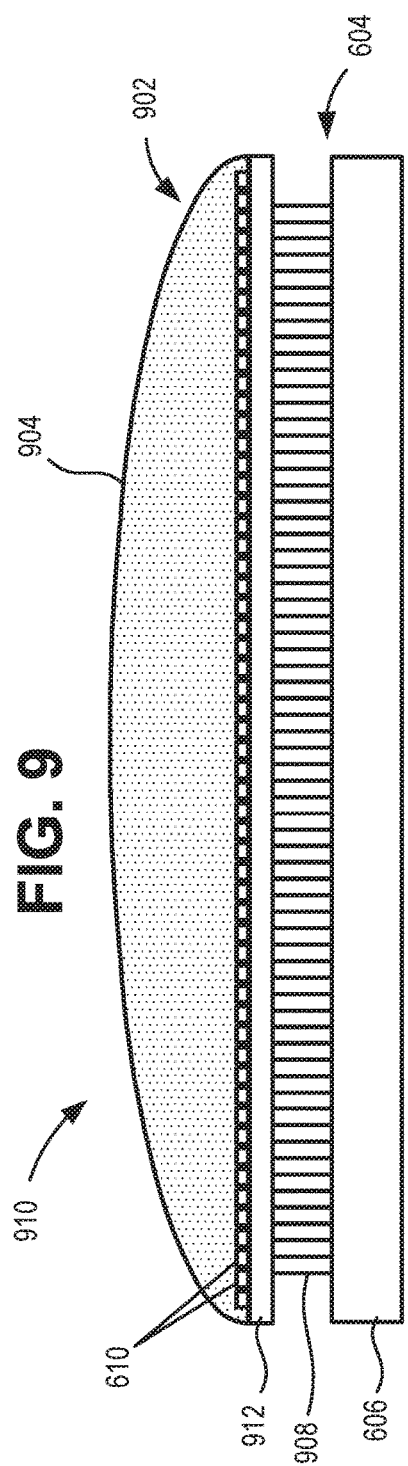
FIG. 9 is a side view of an ultrasound transducer array of the EBUS bronchoscope, according to another implementation.

In contrast with the curved array of FIG. 6, FIG. 9 is an illustration of a cross-sectional view of flat transducer assembly 910, according to another embodiment. As shown in FIG. 9, transducer assembly 910 may include a flat ultrasound transducer array 902 with integrated signal processing electronics 606, and an interconnection 908. Transducer array 902 may include multiple MEMS drums 610 mounted on a flat substrate 912. Transducer assembly 910 may further include a lens 904 that encapsulates MEMS drums 610. Lens 904 may include an encapsulating material for MEMS drums to mechanically focus the array. In one implementation, interconnection 908 may be similar to flexible interconnection 608 In another implementation, interconnection 908 may include a different (e.g., rigid) type of connection between transducer array 902 and signal-processing electronics 606.

Figure 10:
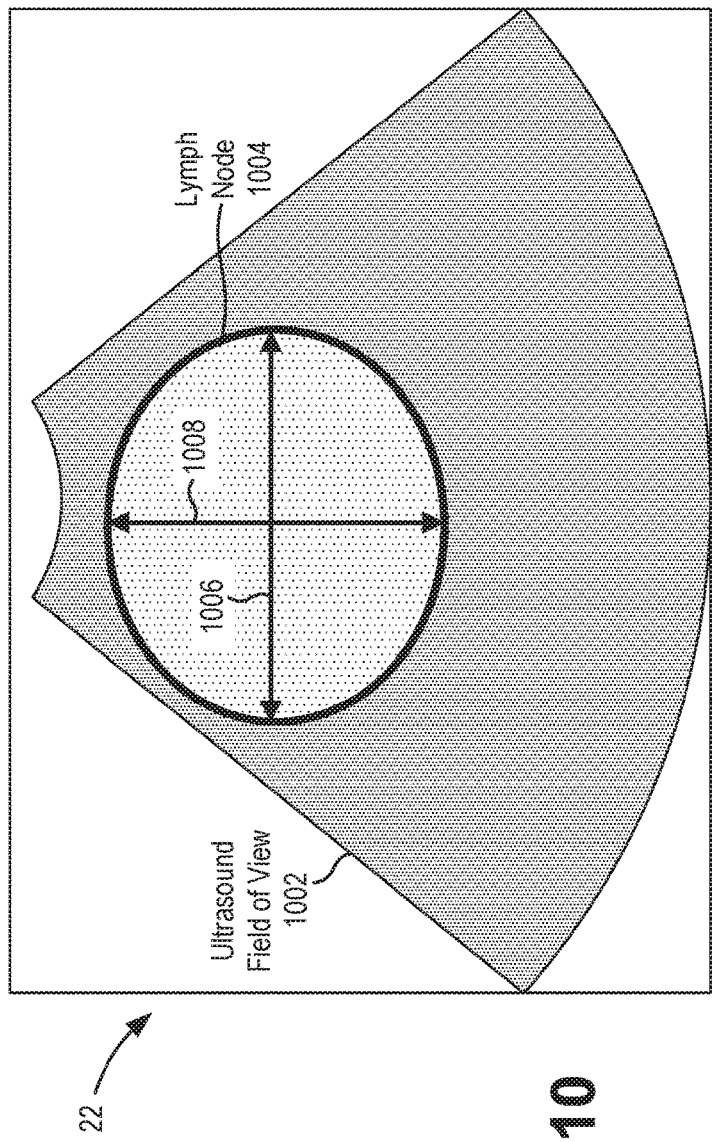
FIG. 10 is an illustration of an ultrasound image of a bronchial lymph node from an EBUS bronchoscope, according to an implementation described herein.

FIG. 10 is an illustration of an ultrasound image of a bronchial lymph node from EBUS bronchoscope 100. An image 1002 may be presented on display 22. Image 1002 may correspond to an ultrasound field of view, which captures a lymph node 1004. Lymph node 1004 is shown with measurements of a long axis 1006 and a short axis 1008. Image characteristics that may be useful for detection of lung cancer, include lymph node size, shape, margin, echogenicity, and other structural details. Exemplary details include whether the lymph node size is less than or greater than one centimeter (along short axis 1008), whether the shape is an oval or a circle, whether the margin is indistinct or distinct, whether the echogenicity is homogenous or inhomogeneous, whether the central hilar structure is present or absent, and whether a coagulation necrosis sign is present or absent. Machine learning algorithms, such as deep learning convolution neural networks, may be used to automate detection of cancer in bronchial lymph nodes.

Figure 11:
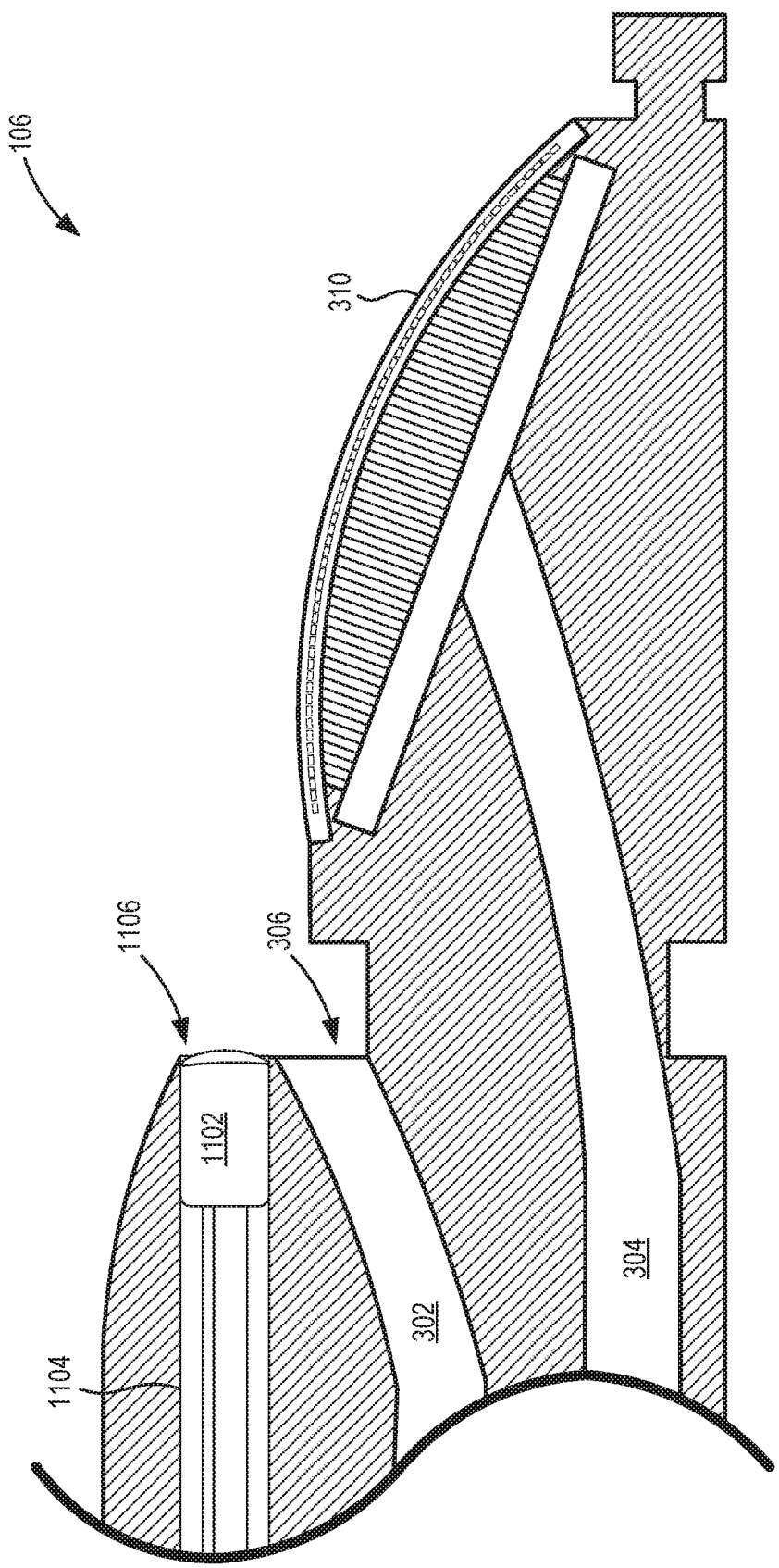
FIG. 11 is a cross sectional side view of distal tip of an EBUS bronchoscope according to another implementation described herein.

FIG. 11 is an illustration of a cross sectional side view of distal tip 106 of EBUS bronchoscope 100 according to another implementation described herein. FIG. 11 illustrates distal tip 106 with a camera module 1102 extending through a camera channel 1104 and out a camera exit port 1106. Camera channel 1104 may extend along the axial length of insertion tube 104 back to handle 102 and connect electrically to the console 20. Camera exit port 1106 may generally point camera module 1102 to view the same area (i.e., of a patient) that would be interrogated by transducer array 602. The views from camera module 1102 and images obtained from transducer assembly 310 may be used in combination to detect and guide insertion of tools (e.g., biopsy needle 504) from working channel lumen 302. For example, EBUS bronchoscope 100 can be used to guide transbronchial needle aspiration (TBNA) for bronchial lymph node biopsy.

Figure 12A:
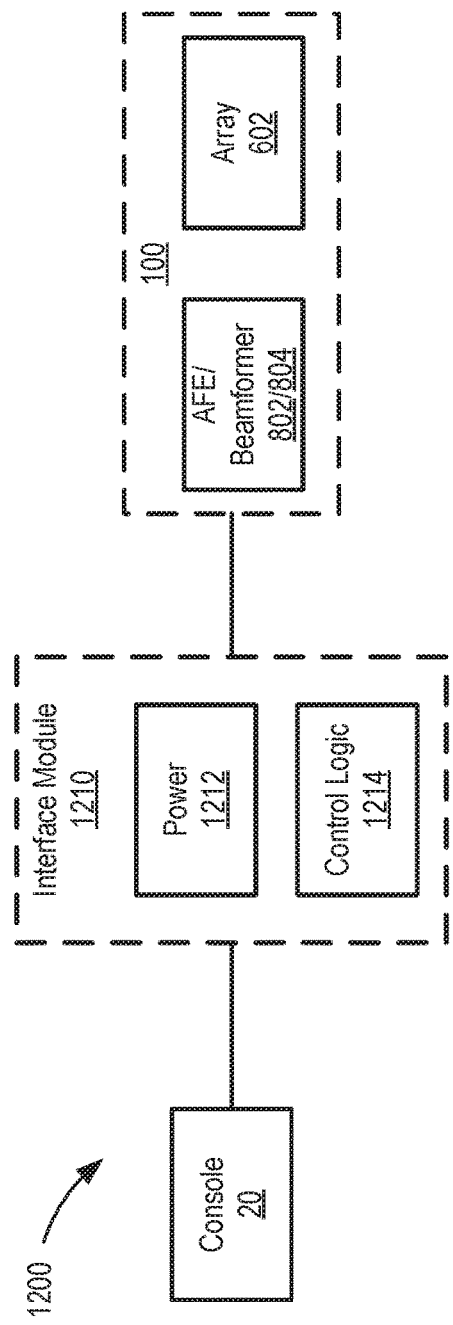
FIGS. 12A and 12B are block diagrams illustrating functional component of EBUS bronchoscope systems according to implementations described herein.
Figure 12B:
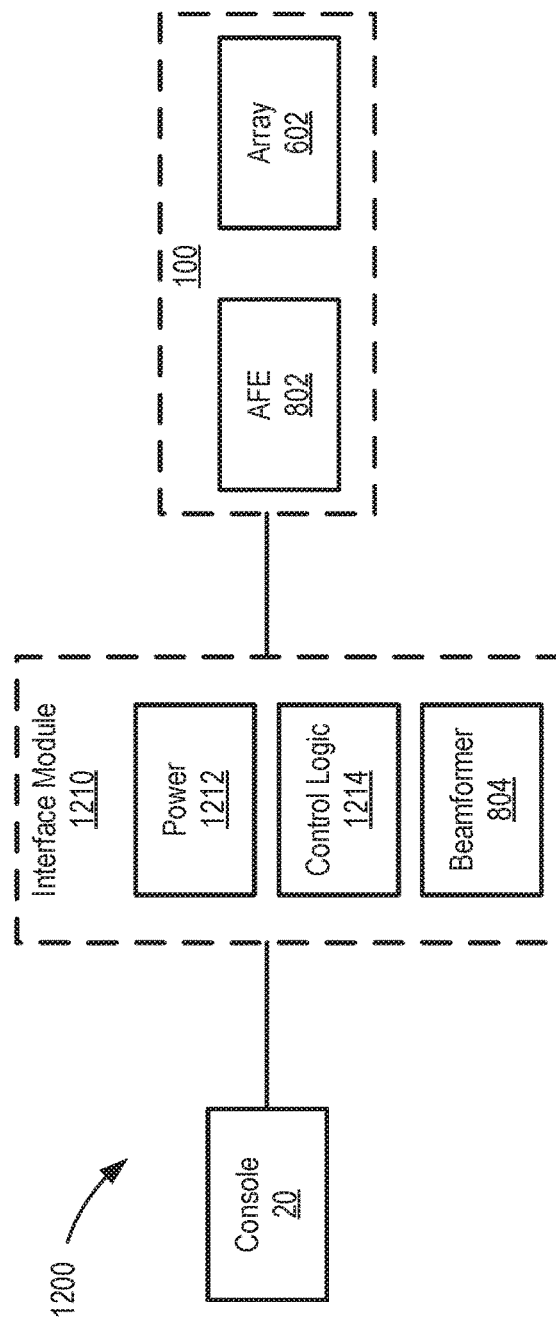

FIGS. 12A and 12B are block diagrams illustrating different arrangements of functional components of an EBUS system 1200 according to implementations described herein. Particularly, FIGS. 12A and 12B illustrate different locations for signal processing electronics 606 (e.g., analog front end 802 and beamformer 804) within EBUS system 1200. As shown in FIGS. 12A and 12B, EBUS system 1200 may include console 20, EBUS bronchoscope 100, and an interface module 1210. Interface module 1210 may be implemented as separate module, integrated within console 20, integrated within handle 102, distributed among a cable and console 20, distributed among multiple consoles, etc.

As shown in FIG. 12A, interface module 1210 may include a power supply 1212 and control logic 1214. Power supply 1212 may include an internal power supply (e.g., rechargeable battery, replaceable battery, etc.), and/or provide connection to an external power supply (e.g., an outlet, AC or DC power, etc.) for components of EBUS bronchoscope 100. Control logic 1214 may provide commands for AFE 802 and beamformer 804 to implement or execute. Control logic 1214 may also control application of power from an external power source (e.g., a charger) to one or more components of EBUS bronchoscope 100.

In the configuration of FIG. 12A, EBUS bronchoscope 100 may include analog front end 802 and beamformer 804 (e.g., signal-processing electronics 606 of FIG. 6) and transducer array 602. For example, analog front end 802, beamformer 804, and transducer array 602 may be included within distal tip 106. Analog front end 802 may, for example, perform multiplexing and other signal processing to transmit and receive ultrasound signals. Beamformer 804 may, for example, adjust phase, frequency, and/or amplitude modulations for the MEMS drums of transducer array 602.

In the configuration of FIG. 12B, EBUS bronchoscope 100 may include analog front end 802 and transducer array 602. For example, analog front end 802 and transducer array 602 may be included within distal tip 106. In the configuration of FIG. 12B, beamformer 804 may function similarly as in the configuration of FIG. 12A. However, beamformer 804 may be located in interface module 1210 (e.g., some signal-processing electronics 606 of FIG. 6 are in different physical locations).

Figure 13:
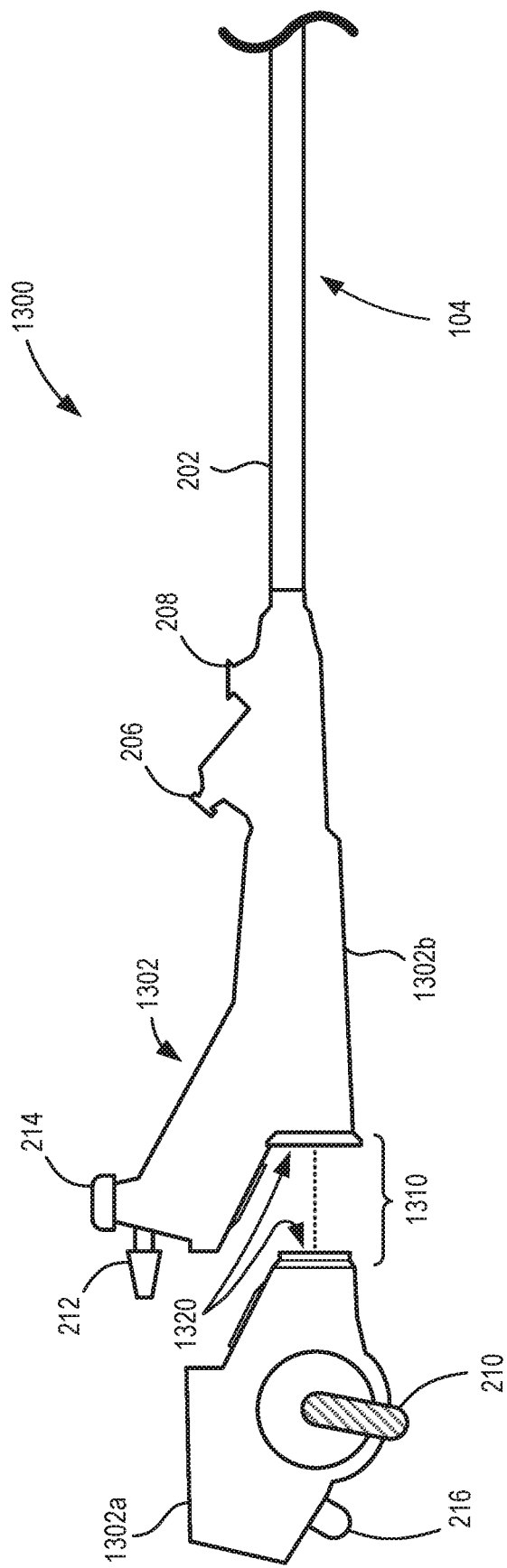
FIG. 13 is a schematic side view of an EBUS bronchoscope with a detachable insertion tube, according to an implementation described herein.

FIG. 13 is a side view of a portion 1300 of EBUS bronchoscope 100, including handle 1302 (comprising segments 1302a and 1302b) and proximal section 202 of insertion tube 104. In the configuration of FIG. 13, handle 1302 may be separated into detachably connected segments 1302a and 1302b through use of a coupling 1310. Generally, handle 1302 may include a linking interface 1320 that allows handle segment 1302b to be attached to handle segment 1302a for a procedure and removed/discarded at the completion of the procedure (e.g., single use of handle segment 1302b and insertion tube 104, with a reusable handle segment 1302a). The separation of handle segments 1302a and 1302b (e.g., at linking interface 1320) is located such that working channel entry port 206, injection port 208, and suction port 212 are included within handle segment 1302b, such that all ports, channels, and/or lumens exposed to bodily fluids during a procedure are included in the disposable components of handle segment 1302b and insertion tube 104.

Linking interface 1320 may include a power cable interface to connect one or more power cables (e.g., cables 308) from imaging core lumen 304 and handle segment 1302b to a power supply (e.g. power supply 1212) accessible in or through handle segment 1302a. Linking interface 1320 may also include a communication interface to connect the communication wires (e.g., cables 308) to wires in handle segment 1302a that lead to control logic (e.g., control logic 1214). In other implementations, linking interface 1320 may provide additional connections for flexion/extension lever 210 to connect to cables 404 extending from flexion/extension cable lumens 406. In one implementation, coupling 1310 may include a mechanical push-on coupling, a threaded coupling, an interference fit coupling, etc.

According to implementations described herein, an endobronchial ultrasound (EBUS) bronchoscope is configured as a single-use (e.g., disposable) device. The bronchoscope includes an insertion tube having a proximal section adjacent the handle and a distal tip. An ultrasound transducer assembly is located at or near the distal tip. The ultrasound transducer assembly includes an ultrasound transducer array, transmit-and-receive circuitry for the ultrasound transducer array, and a flexible interconnection between the ultrasound transducer array and the transmit-and-receive circuitry. The insertion tube further includes an imaging lumen including one or more power cables and one or more communication wires that extend from the ultrasound transducer assembly through the proximal section and a working channel that is separate from the imaging lumen.

According to another implementation, a single-use insertion tube and handle segment may be provided for use with a reusable handle segment. A linking interface is provided for removably connecting a disposable handle segment to the reusable handle segment of the bronchoscope. The linking interface connects one or more power cables to a power supply and connects one or more communication wires to control logic in the handle.

In another embodiment, systems and methods described herein may be applied to an endoscopic ultrasound procedure in other areas of the body (e.g., for upper gastrointestinal tract or lower gastrointestinal tract). More particularly, a MEMS-based ultrasound transducer may integrated with analog and/or digital electronics installed within a distal tip of an endoscope insertion tube in manner similar to that described above.

The systems and methods described herein may provide a disposable EBUS bronchoscope, a disposable bronchoscope insertion tube and handle segment, a disposable endoscope, and/or a disposable endoscope insertion tube and handle segment. By implementing these devices as single-use components, healthcare facilities can avoid the expense, time, and logistics of reprocessing EBUS bronchoscopes and/or endoscopes between uses in different patients. Furthermore, the devices may be supplied fully-assembled in sterile packaging so that separate attachment of some other disposable components, such as inflatable balloons and biopsy needles, is not required.

The foregoing description of exemplary implementations provides illustration and description, but is not intended to be exhaustive or to limit the embodiments described herein to the precise form disclosed. Modifications and variations are possible in light of the above teachings or may be acquired from practice of the embodiments.

Although the invention has been described in detail above, it is expressly understood that it will be apparent to persons skilled in the relevant art that the invention may be modified without departing from the spirit of the invention. Various changes of form, design, or arrangement may be made to the invention without departing from the spirit and scope of the invention.

Certain features described above may be implemented as "logic" or a "unit" that performs one or more functions. This logic or unit may include hardware, such as one or more processors, microprocessors, application specific integrated circuits, or field programmable gate arrays, software, or a combination of hardware and software.

No element, act, or instruction used in the description of the present application should be construed as critical or essential to the invention unless explicitly described as such. Also, as used herein, the article "a" is intended to include one or more items. Further, the phrase "based on" is intended to mean "based, at least in part, on" unless explicitly stated otherwise.

Use of ordinal terms such as "first," "second," "third," etc., in the claims to modify a claim element does not by itself connote any priority, precedence, or order of one claim element over another, the temporal order in which acts of a method are performed, the temporal order in which instructions executed by a device are performed, etc., but are used merely as labels to distinguish one claim element having a certain name from another element having a same name (but for use of the ordinal term) to distinguish the claim elements.

What is claimed is:

1. A bronchoscope, comprising:
a handle; and
an insertion tube having a proximal section adjacent the handle and a distal tip, the insertion tube comprising:
an ultrasound transducer assembly installed within the distal tip, the ultrasound transducer assembly including:
an ultrasound transducer array,
integrated signal processing electronics for the ultrasound transducer array, wherein the integrated signal processing electronics include an analog front end configured to adjust a carrier frequency, acoustic intensity, pulse repeating frequency, signal bias, and gain level of ultrasound signals, and
a flexible interconnection that provides wired connections between the ultrasound transducer array and the analog front end,
an imaging lumen including one or more power cables and one or more communication wires that extend from the ultrasound transducer assembly through the proximal section,
a working channel that is separate from the imaging lumen, and
an inflatable balloon secured over the ultrasound transducer array,
wherein the handle and the insertion tube, with the inflatable balloon secured over the ultrasound transducer array, are enclosed together in a sterile package.

2. The bronchoscope of claim 1, further comprising:
a needle positioned within the working channel and enclosed in the sterile package.

3. The bronchoscope of claim 1, wherein the insertion tube further comprises:
an inflation lumen, the inflation lumen including an exit port configured to provide access to an interior of the balloon when the balloon is secured on the distal tip over the ultrasound transducer array.

4. The bronchoscope of claim 1, wherein the insertion tube further comprises:
a control lumen extending through the proximal section toward the distal tip, and
a control cable extending along a length of the control lumen, wherein the control cable is connected to a steering control element located in the handle.

5. The bronchoscope of claim 1, wherein the insertion tube further comprises:
a camera lumen extending along an axial length of the insertion tube, the camera lumen including a camera exit port near the distal tip.

6. The bronchoscope of claim 1, wherein the ultrasound transducer array includes a curved two-dimensional array.

7. The bronchoscope of claim 1, wherein the ultrasound transducer array includes a microelectromechanical system (MEMS).

8. The bronchoscope of claim 1, further comprising:
a convex lens applied over the ultrasound transducer array.

9. The bronchoscope of claim 1, wherein the integrated signal processing electronics for the ultrasound transducer array further include a beamformer.

10. The bronchoscope of claim 1, wherein the integrated signal processing electronics for the ultrasound transducer array further include a multiplexer.

11. The bronchoscope of claim 1, further comprising:
a linking interface for removably connecting a first handle segment to a second handle segment, wherein the second handle segment includes an entry port for the working channel, and wherein the linking interface:
connects the one or more power cables to a power supply, and
connects the one or more communication wires to control logic.

12. An insertion tube for a bronchoscope, comprising:
a proximal section configured to connect to a handle of the bronchoscope;
a distal tip;
an ultrasound transducer assembly located within the distal tip, the ultrasound transducer assembly including:
an ultrasound transducer array,
integrated signal processing electronics for the ultrasound transducer array, wherein the integrated signal processing electronics include an analog front end configured to adjust at least two of a carrier frequency, acoustic intensity, pulse repeating frequency, signal bias, and gain level of ultrasound signals, and
a flexible interconnection that provides wired connections between the ultrasound transducer array and the analog front end,
an imaging lumen including one or more power cables and one or more communication wires for the ultrasound transducer assembly;
a working channel that is separate from the imaging lumen; and
a sterile needle positioned within the working channel,
wherein the insertion tube and the sterile needle are enclosed together in a sterile package.

13. The insertion tube of claim 12, further comprising:
an inflatable balloon secured over the ultrasound transducer array.

14. The insertion tube of claim 12, wherein the ultrasound transducer array includes a microelectromechanical system (MEMS).

15. The insertion tube of claim 12, wherein the integrated signal processing electronics for the ultrasound transducer array further include a beamformer.

16. The insertion tube of claim 12, further comprising:
a linking interface for removably connecting a first handle segment to a second handle segment, wherein the second handle segment includes an entry port for the working channel, and wherein the linking interface includes:
a power cable interface to connect the one or more power cables to a power supply, and
a communication interface to connect the one or more communication wires to control logic.

17. The bronchoscope of claim 1, wherein at least a portion of the distal tip is located distally beyond an exit port of the working channel.

18. The insertion tube of claim 12, wherein at least a portion of the distal tip is located distally beyond an exit port of the working channel.

* * * * *